United States Patent [19]

Zimmerman et al.

[11] 4,348,488
[45] Sep. 7, 1982

[54] POLYURETHANES USING NOVEL N-SUBSTITUTED PERHYDRODIOXAZEPINES AS CATALYSTS

[75] Inventors: Robert L. Zimmerman; Edward E. McEntire, both of Austin, Tex.

[73] Assignee: Texaco Inc., White Plains, N.Y.

[21] Appl. No.: 300,311

[22] Filed: Sep. 8, 1981

[51] Int. Cl.³ ............................................. C08G 18/20
[52] U.S. Cl. ....................................... 521/115; 528/53
[58] Field of Search .......................... 521/115; 528/53

[56] References Cited

U.S. PATENT DOCUMENTS

| | | | |
|---|---|---|---|
| 3,786,005 | 1/1974 | Bechara et al. | 260/2.5 AC |
| 3,912,689 | 10/1975 | Bechara et al. | 260/75 NC |
| 3,925,268 | 12/1975 | Rosemund et al. | 260/2.5 AC |
| 3,981,829 | 9/1976 | Cenker et al. | 260/2.5 AC |
| 4,011,223 | 3/1977 | Priest et al. | 260/268 R |
| 4,012,445 | 3/1977 | Priest et al. | 260/561 A |
| 4,251,637 | 2/1981 | McEntire et al. | 521/115 |

OTHER PUBLICATIONS

Kapnang, H. and G. Charles, "Perhydro Dioxazepines-1,5,3:Method Generale de Synthese," Tetrahedron Letters, vol. 21, No. 31, 1980, pp. 2949–2950.

Primary Examiner—Maurice J. Welsh
Attorney, Agent, or Firm—Carl G. Ries; Jack H. Park; David L. Mossman

[57] ABSTRACT

A primary amine may be reacted with formaldehyde and a 1,2-diol to produce N-substituted perhydrodioxazepines of the formula

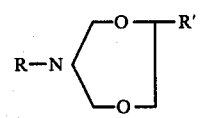

where R is alkyl, alkoxyalkyl, aminoalkyl or aryl alkyl and R' is hydrogen or lower alkyl. These compounds may be easily prepared and have a low odor which is essential in their utility as polyurethane catalysts. By varying the R group, the catalytic characteristics of the compounds may be altered as desired.

12 Claims, No Drawings

POLYURETHANES USING NOVEL N-SUBSTITUTED PERHYDRODIOXAZEPINES AS CATALYSTS

A related application, Ser. No. 300,405, directed to the N-tert-amino-substituted perhydrodioxazepines as novel compounds has been filed of even date.

BACKGROUND OF THE INVENTION

1. Field of the Invention

The invention relates to polyurethanes and the production thereof and more particularly relates to polyurethanes using N-tert-amino-substituted perhydrodioxazepines-1,5,3 as the catalysts.

2. Description of the Prior Art

Perhydrodioxazepines-1,5,3 are known compounds. They may be prepared from primary amines, 1,2-diols and paraformaldehyde according to the method outlined by H. Kapnang and G. Charles in "Perhydro Dioxazepines-1,5,3: Method Generale de Synthese," Tetrahedron Letters, Vol. 21, No. 31, 1980, pp. 2949-2950. This article also discloses a number of N-substituted perhydrodioxazepines, where most of the N-substituents are alkyl groups. It has been surprisingly found that N-substituted perhydrodioxazepines-1,5,3 with other substituents are suitable for use as polyurethane catalysts.

The use of a catalyst in preparing polyurethanes by the reaction of a polyisocyanate, a polyol and perhaps other ingredients is known. The catalyst is employed to promote at least two, and sometimes three major reactions that must proceed simultaneously and competitively at balanced rates during the process in order to provide polyurethanes with the desired physical characteristics. One reaction is a chain extending isocyanate-hydroxyl reaction by which a hydroxyl-containing molecule is reacted with an isocyanate-containing molecule to form a urethane. This increases the viscosity of the mixture and provides a polyurethane containing a secondary nitrogen atom in the urethane groups. A second reaction is a crosslinking isocyanate urethane reaction by which an isocyanate-containing molecule reacts with a urethane group containing a secondary nitrogen atom. The third reaction which may be involved is an isocyanate-water reaction by which an isocyanate-terminated molecule is extended and by which carbon dioxide is generated to blow or assist in the blowing of the foam. The third reaction is not essential if an extraneous blowing agent, such as a halogenated, normally liquid hydrocarbon, carbon dioxide, etc. is employed, but is essential if all or even a part of the gas for foam generation is to be generated by this in situ reaction (e.g. in the preparation of "one-shot" flexible polyurethane foams).

The reactions must proceed simultaneously at optimum balanced rates relative to each other in order to obtain a good foam structure. If carbon dioxide evolution is too rapid in comparison with chain extension, the foam will collapse. If the chain extension is too rapid in comparison with carbon dioxide evolution, foam rise will be restricted, resulting in a high density foam with a high percentage of poorly defined cells. The foam will not be stable in the absence of adequate crosslinking.

It has long been known that tertiary amines, such as trimethylamine, triethylamine, etc., are effective for catalyzing the second crosslinking reaction. Other typical tertiary amines are set forth in U.S. Pat. Nos. 3,925,368; 3,127,436; and 3,243,387 and German OLS Nos. 2,354,952 and 2,259,980. Some of the tertiary amines are effective for catalyzing the third water-isocyanate reaction for carbon dioxide evolution. However, tertiary amines are only partially effective as catalysts for the first chain extension reaction. To overcome this problem, the so-called "prepolymer" technique has been developed wherein a hydroxy-containing polyol component is partially reacted with the isocyanate component in order to obtain a liquid prepolymer containing free isocyanate groups. This prepolymer is then reacted with additional polyol in the presence of a tertiary amine to provide a foam. This method is still commonly employed in preparing rigid urethane foams, but has proven less satisfactory for the production of flexible urethane foams.

For flexible foams, a one-step or "one-shot" process has been developed wherein a tertiary amine, such as triethylenediamine, is employed in conjunction with an organic tin compound. Triethylenediamine is particularly active for promoting the water-isocyanate reaction and the tin compound is particularly active in synergistic combination with the triethylenediamine for promoting the chain extension reaction. However, even here, the results obtained leave much to be desired. Triethylenediamine is a solid and must be dissolved prior to use to avoid processing difficulties. Also, triethylenediamine and other of the prior art amines can impart a strong amine odor to the polyurethane foam.

In addition to problems of odor and handling due to solid character, other tertiary amines suffer still further deficiencies. For example, in some instances the compounds are relatively high in volatility leading to obvious safety problems. In addition, some catalysts of this type do not provide sufficient delay in foaming, which delay is particularly desirable in molding applications to allow sufficient time to situate the preform mix in the mold. Yet other catalysts, while meeting specifications in this area do not yield foams with a desirable tack-free time.

Lastly, while certain tertiary amines are somewhat suitable in this catalytic area they nevertheless do not have a sufficiently high tertiary amine content in terms of the number of tertiary amines compared to overall molecular weight. It is believed that the higher the tertiary amine content the more rapid the catalytic activity in the polyurethane art.

Heterocyclic tertiary amines are known as urethane catalysts, the most well known being perhaps N-ethylmorpholine. Unfortunately, this particular catalyst also has a high amine odor which is transferred to resultant urethane foam, which is undesirable. A number of heterocyclic tertiary amines have recently been found to be catalytically active for polyurethane and polyisocyanurate production. For example, U.S. Pat. No. 4,251,637 shows that tertiary amino substituted oxazolidines are useful as polyisocyanurate catalysts. These materials may be prepared by reacting a tertiary-primary diamine with an olefin oxide and then using a formaldehyde treatment. Beta-aminopropionitriles containing both oxygen and nitrogen in their rings have found utility as urethane catalysts according to U.S. Pat. No. 3,925,268. Utility as a polyurethane catalyst is also found for bis-(1,4-beta-amino carbonyl-ethyl)-piperazines according to U.S. Pat. Nos. 4,011,223 and 4,012,445 and for 4-(2-dimethylaminomethyl) morpholine described in U.S. Pat. No. 3,786,005. Dialkylaminoalkylimidazoles are other heterocyclic tertiary amines useful as urethane catalysts as disclosed in U.S.

Pat. No. 3,912,689. The compounds alkanolaminotriazines and hexahydrotriazines catalyze the creation of carbodiimide and isocyanurate linkages as revealed in U.S. Pat. No. 3,981,829. Other tertiary amines recently found to be useful catalysts which do not contain cyclic portions are described in U.S. Pat. Nos. 4,022,720; 4,026,840; 4,033,911; 4,038,210; and 4,048,107.

SUMMARY OF THE INVENTION

The invention concerns a method for producing a polyurethane which comprises reacting an organic polyisocyanate with an organic polyester polyol or polyether polyol in the presence of a catalytic amount of an N-substituted perhydrodioxazepine of the formula

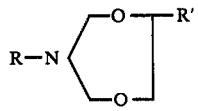

where R is alkyl, alkoxyalkyl, aminoalkyl or arylalkyl and R' is hydrogen or lower alkyl.

DESCRIPTION OF THE PREFERRED EMBODIMENTS

The N-substituted perhydrodioxazepines-1,5,3 of this invention are generally prepared by reacting together a primary amine with a 1,2-diol and formaldehyde. The amine may be added last before the reaction mixture is heated to reflux and the water by-product is azeotroped off. Toluene may be employed as the azeotropic agent.

Any type of primary amine is useful in making N-substituted perhydrodioxazepines-1,5,3. If the N-substituent is to be alkyl, then amines such as isopropylamine, tert-butylamine and cyclohexylamine may be used to make the compounds disclosed by H. Kapnang and G. Charles in "Perhydro Dioxazepines-1,5,3: Method Generale de Synthese," Tetrahedron Letters, Vol. 21, No. 31, 1980 at p. 2950. The compounds of this invention may be made if primary amines such as dimethylaminopropylamine, methoxypropylamine, aminopropylmorpholine, etc. are used. Diprimary amines, such as N,N'-bisaminopropylpiperazine, are also useful to make bis-N-substituted perhydrodioxazepines. The catalytic characteristics of the compounds can be changed by changing the R substituent group as desired.

Also, any 1,2-diol would be useful to prepare the inventive compounds. The most common diols to be used would probably be ethylene glycol and propylene glycol. The formaldehyde component may be introduced as formaldehyde or paraformaldehyde, whichever is most convenient. The following examples will illustrate the preparation of representative compounds of this invention.

EXAMPLE I

Preparation of 3-[3-(dimethylamino)propyl] perhydrodioxazepine-1,5,3

In a one liter flask equipped with a mechanical stirrer was placed 120 g (4 moles) of paraformaldehyde, 62 g (1 mole) of ethylene glycol and 200 ml of toluene. To this mixture was added 204 g (2 moles) of 3-(dimethylamino)propylamine. The reaction was then heated to reflux and the water azeotroped off. After all the water had been removed, the reaction was placed under vacuum and the solvent was stripped off. The product was then distilled under vacuum. Its boiling point was 85°–87° C. at 0.8 mm Hg pressure.

EXAMPLE II

Preparation of 3-(3-methoxypropyl)perhydrodioxazepine-1,5,3

The same procedure as in Example I was used. The amounts of materials were as follows: methoxypropylamine 178 g (2 moles), paraformaldehyde 120 g (4 moles), ethylene glycol 124 g (2 moles) and toluene 400 ml. The product was distilled at 79°–83° C. at 0.35 mm Hg vacuum.

EXAMPLE III

Preparation of 3-(3-morpholinopropyl)-6-methylperhydrodioxazepine-1,3,5

The same procedure as in Example I was used. The amounts of materials used were as follows: 4-(3-Aminopropyl)morpholine 288 g (2 moles), propylene glycol 152 g (2 moles), paraformaldehyde 120 g (4 moles), and toluene 500 ml. The product was distilled at 128°–132° C. at 0.35 mm Hg vacuum.

EXAMPLE IV

Preparation of 1,4-bis[3-(3-perhydrodioxazepinyl-1,5,3)propyl] piperazine

The same procedure as in Example I was used except the product was not distilled. The amounts of materials used were as follows: N,N'-bisaminopropylpiperazine 200 g (1 mole), paraformaldehyde 120 g (4 moles), ethylene glycol 124 g (2 moles), and 1000 ml of toluene.

To prepare polyurethanes using the catalysts here, any aromatic polyisocyanate may be used. Typical aromatic polyisocyanates include m-phenylene diisocyanate, p-phenylene diisocyanate, polymethylene polyphenylisocyanate, 2,4-toluene diisocyanate, 2,6-toluene diisocyanate, dianisidine diisocyanate, bitolylene diisocyanate, naphthalene-1,4-diisocyanate, xylylene-1,4-diisocyanate, xylylene-1,3-diisocyanate, bis(4-isocyanatophenyl)methane, bis(3-methyl-4-isocyanatophenyl)methane, bis(3-methyl-4-isocyanatophenyl)methane, and 4,4'-diphenylpropane diisocyanate.

Greatly preferred aromatic polyisocyanates used in the practice of the invention are 2,4- and 2,6-toluene diisocyanates and methylene-bridged polyphenyl polyisocyanate mixtures which have a functionality of from about 2 to 4. These latter isocyanate compounds are generally produced by the phosgenation of corresponding methylene bridged polyphenyl polyamines, which are conventionally produced by the reaction of formaldehyde and primary aromatic amines, such as aniline, in the presence of hydrochloric acid and/or other acidic catalysts. Known processes for preparing polyamines and corresponding methylene-bridged polyphenyl polyisocyanates therefrom are described in the literature and in many patents, for example, U.S. Pat. Nos. 2,683,730; 2,950,263; 3,012,008; 3,344,162 and 3,362,979.

Most preferred methylene-bridged polyphenyl polyisocyanate mixtures used here contain about 20 to about 100 weight percent methylene diphenyldiisocyanate isomers, with the remainder being polymethylene polyphenyl polyisocyanates having higher functionalities and higher molecular weights. Typical of these are polyphenyl polyisocyanate mixtures containing about 20 to 100 weight percent methylene diphenyldiisocyanate isomers, of which 20 to about 95 weight percent thereof is the 4,4'-isomer with the remainder being polymethylene polyphenyl polyisocyanates of higher molecular weight and functionality that have an average functionality of from about 2.1 to about 3.5. These isocyanate mixtures are known, commercially available materials and can be prepared by the process described in U.S. Pat. No. 3,362,979, issued Jan. 9, 1968 to Floyd E. Bentley.

The hydroxyl-containing polyol component which reacts with the isocyanate may suitably be a polyester polyol or a polyether polyol having a hydroxyl number ranging from about 700 to about 25, or lower. When it is desired to provide a flexible foam, the hydroxyl number is preferably in the range from about 25 to 60. For rigid foams, the hydroxyl number is preferably in the range from 350 to 700. Semi-rigid foams of a desired flexibility are provided when the hydroxyl number is intermediate to the ranges just given.

Also, for a flexible urethane foam the polyol should preferably have an average functionality of from about 2 to about 4 and a molecular weight of from about 2,000 to about 6,000. For rigid foams, the functionality of the polyol component is preferably from about 4 to about 8.

When the polyol is a polyester, it is preferable to use as the polyester, a resin having a relatively high hydroxyl value and a relatively low acid value made from the reaction of a polycarboxylic acid with a polyhydric alcohol. The acid component of the polyester is preferably of the dibasic or polybasic type and is usually free of reactive unsaturation, such as ethylenic groups or acetylenic groups. The unsaturation, such as occurs in the rings of such aromatic acids as phthalic acid, terephthalic acid, isophthalic acid, or the like, is non-ethylenic and non-reactive. Thus, aromatic acids may be employed for the acid component. Aliphatic acids, such as succinic acid, adipic acid, sebacic acid, azelaic acid, etc. may also be employed and are preferred. The alcohol component for the polyester should preferably contain a plurality of hydroxyl groups and is preferably an aliphatic alcohol, such as ethylene glycol, glycerol, pentaerthritol, trimethylolethane, trimethylolpropane, mannitol, sorbitol, or methyl glucoside. Mixtures of two or more of the above identified alcohols may be employed also if desired.

When the hydroxyl-containing component is a polyether polyol for use in flexible polyurethane foam, the polyol may be an alkylene oxide adduct of a polyhydric alcohol with a functionality of from about 2 to about 4. The alkylene oxide may suitably be ethylene oxide, propylene oxide, or 1,2-butylene oxide, or a mixture of some or all of these. The polyol will suitably have a molecular weight within the range of from about 2,000 to about 7,000. For flexible polyether polyurethane foams, the alkylene oxide is preferably propylene oxide or a mixture of propylene oxide and ethylene oxide.

For rigid polyether polyurethane foams, the polyol should have a functionality of from about 4 to about 8 and a molecular weight of from about 300 to about 1,200. Polyols for rigid polyether polyurethane foams may be made in various ways including the addition of an alkylene oxide as above to a polyhydric alcohol with a functionality of from 4 to 8. These polyols may also be, for example, Mannich condensation products of a phenol, an alkanolamine, and formaldehyde, which Mannich condensation product is then reacted with an alkylene oxide (see U.S. Pat. No. 3,297,597).

The amount of hydroxyl-containing polyol compound to be used relative to the isocyanate compound in both polyester and polyether foams normally should be such that the isocyanate groups are present in at least an equivalent amount, and preferably, in slight excess, compared with the free hydroxyl groups. Preferably, the ingredients will be proportioned so as to provide from about 0.9 to about 1.5 mole equivalents of isocyanate groups per mole equivalent of hydroxyl groups. However, for certain shock absorbing foams we have found that by using the catalyst of our invention the mole equivalents of isocyanate to hydroxyl groups can be as low as 0.4.

When water is used, the amount of water, based on the hydroxyl compound, is suitably within the range of about 0.05 mole to about 10.0 moles per mole equivalent of hydroxy compound.

It is within the scope of the present invention to utilize an extraneously added inert blowing agent such as a gas or gas-producing material. For example, halogenated low-boiling hydrocarbons, such as trichloromonofluoromethane and methylene chloride, carbon dioxide, nitrogen, etc. may be used. The inert blowing agent reduces the amount of excess isocyanate and water that is required in preparing flexible urethane foam. For a rigid foam, the use of water is often avoided and the extraneous blowing agent is used exclusively. Selection of the proper blowing agent is well within the knowledge of those skilled in the art. See for example U.S. Pat. No. 3,072,082.

The catalysts discovered here which are useful in the preparation of rigid or flexible polyester or polyether polyurethane foams, based on the combined weight of the hydroxyl-containing compound and polyisocyanate are employed in an amount of from about 0.05 to about 4.0 weight percent. More often, the amount of catalyst used is 0.1–2.0 weight percent.

The catalysts of this invention may be used either alone or in a mixture with one or more other catalysts such as tertiary amines or with an organic tin compound or other polyurethane catalysts. The organic tin compound, particularly useful in making flexible foams may suitably be a stannous or stannic compound, such as a stannous salt of a carboxylic acid, a trialkyltin oxide, a dialkyltin dihalide, a dialkyltin oxide, etc., wherein the organic groups of the organic portion of the tin compound are hydrocarbon groups containing from 1 to 8 carbon atoms. For example, dibutyltin dilaurate, dibutyltin diacetate, diethyltin diacetate, dihexyltin diacetate, di-2-ethylhexyltin oxide, dioctyltin dioxide, stannous octoate, stannous oleate, etc., or a mixture thereof, may be used.

Such tertiary amines include trialkylamines (e.g., trimethylamine, triethylamine), heterocyclic amines, such as N-alkylmorpholines (e.g., N-methylmorpholine, N-ethylmorpholine, etc.), 1,4-dimethylpiperazine, triethylenediamine, etc., and aliphatic polyamines, such as N,N,N'N'-tetramethyl-1,3-butanediamine.

Conventional formulation ingredients are also employed, such as, for example, foam stabilizers, also known as silicone oils or emulsifiers. The foam stabilizer may be an organic silane or siloxane. For example, compounds may be used having the formula:

RSi[O-(R$_2$SiO)$_n$-(oxyalkylene)$_m$R]$_3$ wherein R is an alkyl group containing from 1 to 4 carbon atoms; n is an integer of from 4 to 8; m is an integer of from 20 to 40; and the oxyalkylene groups are derived from propylene oxide and ethylene oxide. See, for example, U.S. Pat. No. 3,194,773.

In preparing a flexible foam, the ingredients may be simultaneously, intimately mixed with each other by the so-called "one-shot" method to provide a foam by a one-step process. In this instance, water should comprise at least a part (e.g. 10% to 100%) of the blowing agent. The foregoing methods are known to those skilled in the art, as evidenced by the following publication: duPont Foam Bulletin, "Evaluation of Some Polyols in One-Shot Resilient Foams," Mar. 22, 1960.

When it is desired to prepare rigid foams, the "one-shot" method or the so-called "quasi-prepolymer method" is employed, wherein the hydroxyl-containing component preferably contains from about 4 to 8 reactive hydroxyl groups, on the average, per molecule.

In accordance with the "quasi-prepolymer method," a portion of the hydroxyl-containing component is reacted in the absence of a catalyst with the polyisocyanate component in proportions so as to provide from about 20 percent to about 40 percent of free isocyanato groups in the reaction product, based on the polyol. To prepare a foam, the remaining portion of the polyol is added and the two components are allowed to react in the presence of catalytic systems such as those discussed above and other appropriate additives, such as blowing agents, foam stabilizing agents, fire retardants, etc. The blowing agent (e.g., a halogenated lower aliphatic hydrocarbon), the foam-stabilizing agent, the fire retardant, etc., may be added to either the prepolymer or remaining polyol, or both, prior to the mixing of the component, whereby at the end of the reaction a rigid polyurethane foam is provided.

Urethane elastomers and coatings may be prepared also by known techniques in accordance with the present invention wherein a tertiary amine of this invention is used as a catalyst. See, for example, duPont Bulletin PB-2, by Remington and Lorenz, entitled "The Chemistry of Urethane Coatings."

The invention will be illustrated further with respect to the following specific examples, which are given by way of illustration and not as limitations on the scope of this invention.

EXAMPLE V

This example illustrates the use of these compounds as catalysts for rigid urethane foams. Quantity amounts are in number of parts by weight.

|  | A | B | C | D |
|---|---|---|---|---|
| Polyol THANOL ® R-480[1] | 35 | 35 | 35 | 35 |
| Silicone L-5420[2] | 0.5 | 0.5 | 0.5 | 0.5 |
| Water | 0.3 | 0.3 | 0.3 | 0.3 |
| Trichlorofluoromethane | 13 | 13 | 13 | 13 |
| Catalyst Example I | 1.0 | — | — | — |
| Catalyst Example II | — | 1.0 | — | — |
| Catalyst Example III | — | — | 1.0 | — |
| Catalyst Example IV | — | — | — | 1.0 |
| MONDUR MR[3] | 51.2 | 51.2 | 51.2 | 51.2 |
| Cream time (seconds) | 18 | 34 | 24 | 27 |
| Gel time (seconds) | 60 | 140 | 117 | 97 |
| Tack free time (seconds) | 80 | 210 | 186 | 161 |
| Rise time (seconds) | 130 | 220 | 229 | 205 |
| Density, lb/ft$^3$ | 1.82 | 1.80 | 1.74 | 1.75 |

[1] A sucrose-amino polyol with a hydroxyl number of 530 sold by Texaco Chemical Co.
[2] A silicone surfactant sold by Union Carbide Corp.
[3] A polymeric isocyanate sold by Mobay Chemical Co.

EXAMPLE VI

This example illustrates the use of these compounds as catalysts for flexible urethane foam.

|  | A | B | C | D |
|---|---|---|---|---|
| THANOL F-3016[1] | 100 | 100 | 100 | 100 |
| Silicone L-6202[2] | 1.1 | 1.1 | 1.1 | 1.1 |
| Water | 4.5 | 4.5 | 4.5 | 4.5 |
| 50% stannous octoate in dioctylphthalate | 0.45 | 0.45 | 0.45 | 0.45 |
| Catalyst Example I | 0.17 | — | — | — |
| Catalyst Example II | — | 0.17 | — | — |
| Catalyst Example III | — | — | 0.17 | — |
| Catalyst Example IV | — | — | — | 0.17 |
| Toluene diisocyanate | 57.3 | 57.3 | 57.3 | 57.3 |
| Index | 1.1 | 1.1 | 1.1 | 1.1 |
| Cream time (seconds) | 11 | 14 | 12 | 10 |
| Rise time (seconds) | 102 | 99 | 99 | 91 |
| Density, lb/ft$^3$ | 1.4 | 1.4 | 1.4 | 1.4 |

[1] An ethoxylated-propoxylated glycerine with a hydroxyl number of 56 sold by Texaco Chemical Co.
[2] A silicone surfactant sold by Union Carbide.

EXAMPLE VII

This example illustrates these compounds are isocyanurate catalysts and that they can be used alone or as a co-catalyst.

|  | A | B | C |
|---|---|---|---|
| Polyol THANOL TR-380[1] | 18.2 | 18.2 | 18.9 |
| Silicone DC-193[2] | 0.5 | 0.5 | 0.5 |
| Trichlorofluoromethane | 13 | 13 | 13 |
| Catalyst Example I | 3.0 | — | 1.0 |
| 50% potassium octoate in a glycol | — | — | 1.0 |
| N,N,N',N'-tetramethyl,1,3-propanediamine | — | 3.0 | — |
| MONDUR MR[3] | 64.3 | 64.3 | 66.7 |
| Index | 5 | 5 | 5 |
| Cream time (seconds) | 5 | 3 | 3 |
| Tack free time (seconds) | 90 | * | 15 |
| Rise time (seconds) | 110 | * | 30 |

[1] Ethoxylated aniline with a hydroxyl number of 295 sold by Texaco Chemical Co.
[2] Silicone surfactant sold by Dow-Corning Corp.
[3] A polymeric isocyanate sold by Mobay Chemical Co.
*The foam did not cure as it rose only part way.

Foams A and B illustrate that the compounds of this invention are good isocyanurate catalysts while ordinary amines are not. Foam C shows its use as a co-catalyst.

Examples V through VII have shown that the novel compounds of this invention are useful as urethane catalysts. It may also be seen that the catalyst characteristics change with the N-substituents.

We claim:
1. A method for producing a polyurethane which comprises reacting an organic polyisocyanate with an organic polyester polyol or polyether polyol in the presence of a catalytic amount of an N-substituted perhydrodioxazepine of the formula

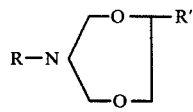

where R is alkyl, alkoxyalkyl, aminoalkyl or aryl alkyl and R' is hydrogen or lower alkyl.

2. The method of claim 1 wherein the polyurethane is a cellular polyurethane obtained by reacting said polyols with said polyisocyanate in the presence of a blowing agent.

3. The method of claim 1 wherein a flexible urethane foam is produced.

4. The method of claim 1 wherein a rigid urethane foam is produced.

5. The method of claim 1 wherein the N-substituted perhydrodioxazepine serves as a isocyanurate catalyst.

6. The method of claim 1 where R is limited to a tertiary amino alkyl radical.

7. The method of claim 1 wherein a flexible polyether polyurethane foam is provided which comprises reacting in the presence of a blowing agent said organic polyisocyanate with a polyether polyol formed by the addition of a polyhydric alcohol having a functionality of from 2 to about 4 with an alkylene oxide of 2 to 4 carbon atoms in the presence of said catalyst, said organic polyisocyanate being employed in an amount sufficient to provide 0.4 to 1.5 mole equivalents of isocyanate groups per mole equivalent of hydroxyl groups, said polyether polyol having a molecular weight within the range of about 2,000 to 7,000.

8. The method of claim 1 wherein a flexible polyester polyurethane foam is prepared which comprises reacting in the presence of a blowing agent toluene diisocyanate with a hydroxyl terminated condensation product of a polycarboxylic acid and a polyhydric alcohol in the presence of said catalyst, said toluene diisocyanate being employed in an amount sufficient to provide 0.9 to 1.5 mole equivalents of isocyanate groups per mole equivalent of hydroxyl groups, said condensation product having a functionality of from about 2 to about 4, and a molecular weight from about 2,000 to about 6,000 and a hydroxyl number ranging from about 25 to about 60.

9. The method of claim 1 wherein said catalyst is 3-[3-(dimethylamino)propyl]perhydrodioxazepine-1,5,3.

10. The method of claim 1 wherein said catalyst is 3-(3-methoxypropyl)perhydrodioxazepine-1,5,3.

11. The method of claim 1 wherein said catalyst is 3-(3-morpholinopropyl)-6-methylperhydrodioxazepine-1,3,5.

12. The method of claim 1 wherein said catalyst is 1,4-bis[3-(3-perhydrodioxazepinyl-1,5,3)propyl]piperazine.

* * * * *